United States Patent
Carr

(10) Patent No.: US 10,101,288 B2
(45) Date of Patent: Oct. 16, 2018

(54) WIRELESS IMPEDANCE SPECTROMETER

(71) Applicant: William N. Carr, Raleigh, NC (US)

(72) Inventor: William N. Carr, Raleigh, NC (US)

( * ) Notice: Subject to any disclaimer, the term of this patent is extended or adjusted under 35 U.S.C. 154(b) by 0 days.

(21) Appl. No.: 15/507,215

(22) PCT Filed: Aug. 28, 2015

(86) PCT No.: PCT/US2015/047595
§ 371 (c)(1),
(2) Date: Feb. 27, 2017

(87) PCT Pub. No.: WO2016/033561
PCT Pub. Date: Mar. 3, 2016

(65) Prior Publication Data
US 2017/0248533 A1 Aug. 31, 2017

Related U.S. Application Data

(60) Provisional application No. 62/210,888, filed on Aug. 27, 2015, provisional application No. 62/106,805, (Continued)

(51) Int. Cl.
*G01N 27/02* (2006.01)
*G01R 15/14* (2006.01)
(Continued)

(52) U.S. Cl.
CPC ............ *G01N 27/02* (2013.01); *G01N 27/026* (2013.01); *G01R 15/146* (2013.01); *G01N 22/00* (2013.01);
(Continued)

(58) Field of Classification Search
CPC ............ G01R 29/0814; G01R 29/0878; G01R 31/002; G01N 22/04; G01N 22/00
(Continued)

(56) References Cited

U.S. PATENT DOCUMENTS 3,694,737 A * 9/1972 Busker ................ G01N 22/04
324/632
3,715,667 A * 2/1973 Nicolson ............. G01N 22/02
324/632
(Continued)

FOREIGN PATENT DOCUMENTS

EP 2275805 A1 1/2011
WO 2008069753 A1 6/2008

OTHER PUBLICATIONS

Authorized Officer: Ruchaud, Nicolas, "International Search Report" issued in counterpart PCT application No. PCT/US2015/047595, dated Nov. 11, 2015, Publisher: PCT.
(Continued)

*Primary Examiner* — Christopher McAndrew
(74) *Attorney, Agent, or Firm* — Kaplan Breyer Schwarz, LLP

(57) ABSTRACT

A system and method for measuring the permittivity and/or the impedance of a material are based on transmitting a first RF signal to a transponder coupled to the material. The transponder is equipped with a resonant antenna coupled to the material such that the response of the antenna is affected by the material. The signal strength of a second RF signal transmitted by the transponder in response to the first RF signal, and received by an interrogator, is measured. The interrogator can calculate both the real part and the imaginary part of the complex impedance of the material from multiple measurements of the signal strength of the second RF signal taken at a plurality of frequencies of the first RF signal.

18 Claims, 7 Drawing Sheets

Related U.S. Application Data filed on Jan. 23, 2015, provisional application No. 62/043,376, filed on Aug. 28, 2014.

(51) Int. Cl.
| | | |
|---|---|---|
| G01R 29/08 | (2006.01) | |
| G01N 22/00 | (2006.01) | |
| G01R 31/00 | (2006.01) | |

(52) U.S. Cl.
CPC ...... *G01R 29/0814* (2013.01); *G01R 29/0878* (2013.01); *G01R 31/002* (2013.01)

(58) Field of Classification Search
USPC ........................................................ 324/632
See application file for complete search history.

(56) References Cited

U.S. PATENT DOCUMENTS

| | | | | |
|---|---|---|---|---|
| 5,187,443 | A * | 2/1993 | Bereskin | G01R 1/0408 324/632 |
| 5,500,599 | A * | 3/1996 | Stange | G01N 22/00 324/632 |
| 6,691,563 | B1 | 2/2004 | Trabelsi et al. | |
| 6,839,035 | B1 * | 1/2005 | Addonisio | G06K 7/10178 340/572.1 |
| 7,315,173 | B2 * | 1/2008 | Funato | G01R 29/0814 324/452 |
| 7,336,230 | B2 * | 2/2008 | Lee | G01R 29/0828 324/627 |
| 8,542,122 | B2 * | 9/2013 | Goodnow | A61B 5/14532 340/572.1 |
| 9,460,320 | B2 * | 10/2016 | Ieki | G06K 7/0008 |
| 2004/0089058 | A1 | 5/2004 | De Haan et al. | |
| 2005/0017727 | A1 | 1/2005 | Oberle | |
| 2007/0146138 | A1 * | 6/2007 | Phipps | G06K 7/0008 340/572.7 |
| 2007/0262869 | A1 * | 11/2007 | Young | G06K 7/10336 340/572.7 |
| 2008/0303717 | A1 * | 12/2008 | Durban | G01S 1/44 342/371 |
| 2010/0090802 | A1 | 4/2010 | Nilsson et al. | |
| 2010/0161004 | A1 * | 6/2010 | Najafi | A61N 1/3787 607/60 |
| 2010/0231407 | A1 * | 9/2010 | Carr | G06K 19/0723 340/691.1 |
| 2010/0271188 | A1 * | 10/2010 | Nysen | G01S 13/755 340/10.41 |
| 2012/0001730 | A1 * | 1/2012 | Potyrailo | G06K 7/10009 340/10.1 |
| 2012/0004851 | A1 * | 1/2012 | Potyrailo | G01N 33/0073 702/19 |
| 2012/0190310 | A1 * | 7/2012 | Ieki | G06K 7/0008 455/73 |
| 2012/0256733 | A1 * | 10/2012 | Carr | G06K 19/0723 340/10.51 |
| 2012/0286935 | A1 * | 11/2012 | Huang | G01D 21/00 340/10.1 |
| 2013/0109305 | A1 * | 5/2013 | Savoj | G06K 7/0008 455/41.1 |
| 2013/0154847 | A1 | 6/2013 | Potyrailo et al. | |
| 2014/0028327 | A1 | 1/2014 | Potyrailo et al. | |
| 2014/0182363 | A1 * | 7/2014 | Potyrailo | G01N 27/026 73/64.53 |

OTHER PUBLICATIONS

Authorized Officer: Ruchaud, Nicolas, "Written Opinion" issued in counterpart PCT application No. PCT/US2015/047595, dated Nov. 11, 2015, Publisher: PCT.

"Dielectric spectroscopy—definition", Retrieved from https://en.wikipedia.org/w/index.php?title=Dielectric_spectroscopy&oldid=670841315, dated Jul. 10, 2015, pp. 1-5, Publisher: Wikimedia Foundation, Inc., Published in: US.

"Wave impedance—definition", Retrieved from 'https://en.wikipedia.org/w/index.php?title=Wave_impedance&oldid=663396976', dated May 21, 2015, pp. 1-3, Publisher: Wikimedia Foundation, Inc., Published in: US.

Pandey et al., "A low RF-band impedance spectroscopy based sensor for in-situ, wireless soil sensing", "Sensors Journal", IEEE; ISSN :1530-437X, dated Feb. 20, 2014, pp. 1997-2005, vol. 14, No. 6, Publisher: IEEE Sensors Council; DOI: 10.1109/JSEN.2014.2307001, Published in: US.

Suwalak et al., "Determination of Dielectric Property of Construction Material Products Using a Novel RFID Sensor", "Progress in Electromagnetics Research", dated 2012, pp. 601-617, vol. 130.

Hasan et al., "A Monopole-Coupled RFID Sensor for Pervasive Soil Moisture Monitoring", "Antennas and Propagation Society International Symposium (APSURSI), 2013 IEEE", dated Jul. 2013, pp. 2309-2310, Publisher: IEEE; ISBN: 978-1-4673-5315-1, Published in: US.

Siden et al., "Remote Moisture Sensing utilizing Ordinary RFID Tags", "IEEE Sensors 2007 Conference", dated 2007, vol. 1-3, Publisher: IEEE.

"Office Action" issued in related U.S. Appl. No. 14/839,876, dated Jan. 22, 2016, Publisher: USPTO.

"Proposed Examiner's Amendment" issued in related U.S. Appl. No. 14/839,876, dated Jan. 15, 2016, Publisher: USPTO.

\* cited by examiner

Impedance spectroscopy

Noninvasive material testing via RFID tag

Antenna response for different values of the real part of the permittivity

Antenna response for different values of the imaginary part of the permittivity System 500 for remote measurement of both real and imaginary components of the impedance of a material System 600 with reference transponder System 700 with tunable transponder System 900 with transponder equipped with range extender

WIRELESS IMPEDANCE SPECTROMETER

CROSS REFERENCE TO RELATED APPLICATIONS

The underlying concepts, but not necessarily the language, of the following cases are incorporated by reference:
(1) U.S. provisional application No. 62/043,376;
(2) U.S. provisional application No. 62/106,805; and
(3) U.S. provisional application No. 62/210,888.
If there are any contradictions or inconsistencies in language between this application and one or more of the cases that have been incorporated by reference that might affect the interpretation of the claims in this case, the claims in this case should be interpreted to be consistent with the language in this case.

This case claims benefit of the following provisional applications:
(1) U.S. provisional application No. 62/043,376;
(2) U.S. provisional application No. 62/106,805; and
(3) U.S. provisional application No. 62/210,888.

FIELD OF THE INVENTION

The present invention relates to wireless sensors in general, and, more particularly, to wireless sensors based on Radio-Frequency IDentification (RFID) technology.

BACKGROUND

There are many practical situations where it is advantageous to learn certain physical characteristics of a material medium without damaging the medium itself. For example, a civil engineer that is building a bridge might want to test the concrete blocks to be used in the bridge to make sure that they meet specifications before installing them, or a farmer might want to learn the moisture content of soil before deciding how much water needs to be used for irrigation. A well established technique for noninvasive material testing is known as impedance spectroscopy, also referred to as dielectric spectroscopy.

FIG. 1 depicts, in schematic form, a simplified implementation of impedance spectroscopy in the prior art. The material to be tested is placed between the two parallel plates of an electrical capacitor, depicted as capacitor plate 120-1 and 120-2 in the figure. This arrangement makes it possible to subject the material to an electric field by applying a voltage to the two plates.

The response of a material to an applied electric field is, in general, a consequence of the material's physical make-up. Such response is usually characterized as a parameter known as the "electrical permittivity" (hereinafter just "permittivity"). For example, the permittivity of soil varies substantially as a function of the amount of moisture in the soil. Similarly, the permittivity of concrete and other construction materials reflects both the composition of the material as well as its condition. It is well known that concrete might exhibit degradation due to environmental factors, and a measurement of the permittivity of concrete can provide information about the concrete's age and integrity.

In FIG. 1, the material to be tested is subjected to a time-varying electric field by connecting the capacitor plates to an "alternating-current" (AC) voltage source, depicted as AC voltage source 130. Note that identification of a voltage source as an "alternating-current" source is, strictly speaking, a misnomer because a voltage source generates a specific voltage, not a current; however, the "AC" abbreviation is commonly used in the art to refer to any source of electrical voltage or current whose output varies as a sinusoidal function of time. An AC source is characterized by an amplitude, which can be expressed in Volts for a voltage source, and a frequency, which can be expressed in Hz.

When AC voltage source 130 applies a specific AC voltage to the capacitor plates, an AC current flows through the circuit, depicted by an arrow as AC current 140 in the figure. The current can be characterized by an amplitude, which can be expressed in Amperes, and a phase, which can be expressed in radians or in angular degrees. The combination of amplitude and phase can be represented as a single quantity by a complex number. It is well known in the art how to use complex numbers for characterizing the behavior of AC circuits and devices.

The complex value of AC current 140 is strongly dependent on the permittivity of material 110. Therefore, measuring the complex value of AC current 140 provides information about the permittivity of the material and, thereby, the condition of the material itself.

Because the voltage applied by AC voltage source 130 and the AC current 140 are both conveniently represented by complex numbers, the permittivity is also conveniently represented by a complex number. In particular, the imaginary part of the permittivity reflects the fact that some of the energy generated by AC voltage source 130 is dissipated inside material 110, and the value of the imaginary part reflects the extent of the dissipation (also commonly referred to as "loss"). Conversely, the real part of the permittivity reflects the fact that some of the energy generated by AC voltage source 130 is stored, without loss, inside material 110. Such stored energy is released by the material at a time different from the time when it was absorbed. The released energy can flow back to AC voltage source 130; or it can be dissipated inside the material, thereby reducing the energy that AC voltage source must deliver.

A feature of an AC voltage source is, of course, that the instantaneous voltage oscillates sinusoidally. As the instantaneous voltage generated by AC voltage source 130 oscillates, the flow of energy out of (or into) AC voltage source 130 is different at different points in the oscillation cycle, and the details depend on the relative strengths of the two physical phenomena, storage and dissipation, characterized by the real and imaginary parts of the permittivity. The full complex value of the AC current 140 reflects these details and provides the necessary information for calculating both the real part and the imaginary part of the permittivity.

Inside a material, energy storage and dissipation are generally mediated by different underlying physical phenomena. Therefore, to achieve a complete characterization of the dielectric properties of a material, it is important to measure the full complex permittivity by independently measuring both the real part and the imaginary part.

Impedance spectroscopy, as depicted in FIG. 1, is advantageous because it yields an estimate of both real and imaginary parts of the complex permittivity. However, the requirement that the material be placed between the plates of a capacitor is a significant obstacle to noninvasive testing of materials in the field. For example, the civil engineer that wants to periodically test the conditions of the concrete in a bridge, after it's built, cannot easily collect samples of the concrete for testing in a lab equipped with an impedance spectrometer without damaging the bridge. Similarly, a farmer that wants to know the moisture contents of soil at a certain depth below the surface, would very much like to be able to do so without having to dig a hole to collect a soil sample. A noninvasive way of remotely testing a material in the field would be very advantageous.

FIG. 2 depicts a system known in the prior art for performing noninvasive material testing. The system is described by H. E. Nilsson, U.S. Published Patent Application 2010/0090802 A1 (hereinafter "Nilsson"). The system takes advantage of so-called Radio-Frequency IDentification (RFID) technology which provides simple, small, low-cost RFID tags that can be queried by an RFID reader via a radio signal.

In the depiction of FIG. 2, an RFID tag 220 is embedded inside the material 210 to be tested. The RFID tag is equipped with a radio antenna 230 for receiving and transmitting Radio-Frequency (RF) signals. An RFID reader 240 located outside of the material to be tested transmits RF signal 255 via its radio antenna 250. The RF signal 255 penetrates the material 210 and reaches antenna 230. The RFID tag responds to the RF signal by transmitting a second RF signal 265, which is received by the RFID reader.

Many techniques are known in the art for RFID tag 220 to generate the response RF signal 265; however, the technique known as backscatter modulation is often preferred because it leads to a simple and inexpensive design for the RFID tag. With backscatter modulation, RF signal 255 is simply reflected by antenna 230, to generate RF signal 265. Such reflection can be accomplished by connecting antenna 230 to an electronic component that reflects back the signal received by the antenna. Electronic circuitry inside the RFID tag can control how the reflecting component reflects the signal, such that the reflectivity of the component can be modulated in accordance with information that the RFID tag wants to convey to the RFID reader.

Through backscatter modulation, the RFID tag accomplishes an important goal: the reflected RF signal 265 is modulated with a unique pattern that uniquely identifies the reflected RF signal 265 as originating from RFID tag 220. This unique pattern enables the RFID reader to extract the reflected RF signal 265 from the clutter of other reflected signals that might be reflected by other objects in the vicinity, including, possibly, other RFID tags.

The ability to extract RF signal 265 from unwanted clutter, allows RFID reader 240 to obtain a good estimate of the signal strength of RF signal 265. Such signal strength is strongly affected by the presence of material 210, and by the material's response to RF signals. In particular, the permittivity of material 210 has a strong influence on ease of propagation of RF signals through the material, such that the signal strength of RF signal 265, as received by RFID reader 240 carries information about the permittivity of material 210.

Unfortunately, as mentioned in previous paragraphs, the permittivity of a material is, in general, a complex number characterized by a real part and an imaginary part. The single measurement of signal strength performed by RFID reader 240 in FIG. 2, provides valuable information about the permittivity of material 210, but it is fundamentally impossible to derive the values of two independent unknown quantities from a single measurement. Therefore, it is impossible, with the system of FIG. 2, to independently estimate the values of both the real part and the imaginary part of the permittivity from just the one measurement of signal strength of RF signal 265. As such, the system of FIG. 2 cannot provide a full characterization of the permittivity of material 210. Clearly, there is a need for a noninvasive way of estimating both real and imaginary parts of the permittivity of a material in the field.

SUMMARY

An antenna for receiving and transmitting RF signals is most conveniently designed as a resonant structure. Such an antenna provides optimal performance at a particular frequency known as the resonant frequency of the antenna, and the antenna itself is referred to as a resonant antenna. The response of a resonant antenna to RF signals is affected by the medium in which the antenna is embedded. In particular, because RF signals are electromagnetic waves, the electric and magnetic properties of the medium are relevant.

When the medium is a material, the electrical permittivity, the magnetic permeability, and the electrical conductivity of the material are the relevant material parameters that determine the response of a resonant antenna to RF signals. The material's properties can be summarized by a material parameter known as the "wave impedance" (or, simply, "impedance") of the material, which is a complex number. A good discussion of the relationship between wave impedance and permittivity, permeability, and conductivity is available, at the time of writing this disclosure, in the Wikipedia entry for wave impedance: http://en.wikipedia.org/wiki/Wave_impedance.

Many materials of interest are nonconductive and nonmagnetic. For such materials, permeability and conductivity do not play a role, and there is a simple, one-to-one relationship between the impedance of the material and the material's permittivity, such that measuring the permittivity and measuring the impedance of the material are equivalent. That is why impedance spectroscopy is also often referred to as dielectric spectroscopy, wherein the adjective "dielectric" refers to the permittivity. For such materials, measurements of the complex impedance yield useful estimates of the complex permittivity, and vice versa. In this disclosure, it is assumed that the materials being tested fall in this category.

Both the real and imaginary parts of the permittivity affect the response of a resonant antenna, but in different ways. A system that measures antenna response at just one frequency cannot distinguish between the two, but a system that uses RF signals at a plurality of frequencies to probe the response of a resonant antenna can collect enough information to distinguish between the two effects and, thereby, independently calculate estimates for the real part and the imaginary part of the permittivity.

Some embodiments of the present invention comprise a transponder embedded in the material to be tested. The transponder comprises a resonant antenna coupled to the material such that the response of the antenna is affected by the material. In particular, a resonant antenna is often characterized in terms of its resonant frequency and its quality factor. The quality factor is primarily affected by energy dissipation and, as such, is strongly dependent on the imaginary part of the permittivity. Conversely, the resonant frequency is more affected by the real part of the permittivity.

The functionality of the transponder can be implemented with techniques similar to those used for RFID tags. In particular backscatter modulation can be used to enable the transponder to receive an RF signal and to transmit a second RF signal in response.

Embodiments of the present invention also comprise an interrogator capable of generating the RF signal intended for reception by the transponder. In some embodiments, the interrogator comprises a multiple frequency generator capable of generating a plurality of frequencies of the transmitted RF signal. The response of the transponder is then measured for multiple frequencies of the RF signal, and the measurements are processed by an impedance calculator that calculates both the real part and the imaginary part of the complex impedance of the material.

The use of multiple frequencies is effective because some frequencies can chosen to be near the resonant frequency of the resonant antenna, while other frequencies can be away from the resonant frequency. The combination of measurements in these two frequency regions can be advantageous for accurately estimating both the real and the imaginary part of the impedance.

In some situations, it is not possible to perform measurements at a wide variety of frequencies. For example, regulatory constraints might make it impossible to transmit RF signals in certain frequency bands. Since what matters is where the frequencies of the RF signal are relative to the resonant frequency of the antenna, alternative embodiments of the present invention are possible wherein the interrogator transmits an RF signal at only one frequency.

In some such embodiments, the transponder is equipped with an antenna tuner that can tune the resonant frequency of the antenna to a plurality of frequencies. Use of the antenna tuner achieves the same result as use of the multiple frequency generator in the interrogator: by tuning the resonant frequency of the antenna to be near the frequency of the RF signal at one time, and away from the frequency of the RF signal at another time, it is possible to obtain measurements of antenna response in the two abovementioned frequency regions.

A tunable transponder, while effective, is more complex and, therefore, more expensive than a non-tunable transponder. It is conceivable that the cost of two or more non-tunable transponders might be less than the cost of a single tunable transponder. If so, alternative embodiments of the present invention are possible wherein the interrogator transmits an RF signal at only one frequency, but non-tunable transponders are used.

In such embodiments, two or more non-tunable transponders are embedded in the material near one another. The transponders have resonant antennas with different resonant frequencies. The frequencies are selected such that some of them are near the frequency of the RF signal, while others are away from the frequency of the RF signal. Because the transponders are near one another, their antennas are affected by the material in similar ways, and, therefore, measurements of signals from different transponders provide the desired measurements in the two frequency regions.

In embodiments of the present invention, calculation of material impedance is based on measurements of the signal strength of the RF signal or signals received by the interrogator. This is an important advantage of embodiments of the present invention, compared to, for example, impedance spectroscopy as depicted in FIG. 1. In that figure, it is necessary to measure both the amplitude and the phase of AC current 140. While it is well known in the art how to perform such measurements, it is often true that a simple signal-strength measurement is easier to perform with simple, low-cost electronics. Therefore, embodiments of the present invention wherein both the real and imaginary parts of the impedance are calculated from simple measurements of signal strength are advantageous in that they allow simpler implementations.

As with any measurements, the accuracy of the final results depends on the accuracy of the measurements. Therefore, in embodiments of the present invention, it is important to obtain accurate measurements of signal strength. The signal strength of a received RF signal is affected by many factors that are not related to the material. For example the distance between the interrogator and the transponder has a strong influence on received signal strength. It is important to characterize such factors so that their effect can be removed from the measurements. Such process is often referred to as "calibration".

Some embodiments of the present invention achieve calibration by performing a set of measurements when the material to be tested in a known state, referred to as a "reference state". For example, the civil engineer knows that, immediately after the bridge is built, the concrete is in good condition. When the bridge was under construction, transponders were embedded in the concrete at places where material tests were expected to be useful in the future. Immediately after completion of bridge construction, the state of the concrete can be regarded as a reference state, and the civil engineer can use an interrogator to obtain measurements of signal strengths from all the transponders. Years later, the engineer can repeat those measurements and the changes in received signal strengths will reflect any deterioration of the concrete that might have occurred.

In the case of construction materials, it is especially advantageous to use embodiments of the present invention to monitor the condition of the material not only as it ages and deteriorates, but also during the construction phase. After being poured, concrete and other construction materials need time to harden and reach the desired physical specifications. During this time, the material's permittivity changes and reflects the progress of the chemical reactions that finally achieve the desired physical specifications. Being able to monitor the permittivity during this time can be very valuable for estimating when the process is complete and when a particular load can be applied to a structure. For example, in the case of a bridge, it might be advantageous to be able to confirm with direct permittivity measurements that the bridge is ready to accept vehicular traffic. Also, the full set of measurements collected while the construction material hardens can provide a more complete and accurate "reference state" than just a single measurement.

In many applications, it might be useful for transponders to also comprise sensors for material parameters other than permittivity. For example, and without limitation, such parameters might comprise material movement, cracking, corrosion and temperature. Through such transponders, it is possible to observe correlations between permittivity changes and changes in other physical parameters of the material, and these can be used to achieve more accurate calibration of permittivity measurements, as well as other benefits. For example, and without limitation, a transponder for soil moisture monitoring that comprises a temperature sensor can provide more accurate measurements when calibrated for the temperature range of interest.

In the examples of the previous paragraphs, when measurements are repeated years after the "reference state" measurements, it is useful to be able to place the interrogator in exactly the same positions where it had been placed for the initial reference measurements, so as to avoid changes in received signal strength due to differences in the distance between the interrogator and the transponders. Several techniques are available for achieving that result. For example, the interrogator might be mounted on a flying drone. Techniques such as GPS positioning and inertial navigation are well established for accurately and repeatably positioning a drone.

An additional advantage of using a drone-mounted interrogator, when examining a structure such as a bridge, is that the drone can carry the interrogator very close to the transponders. This capability not only reduces the risk of signal strength being affected by signal-propagation impairments such as obstacles or multipath, but also makes it easier to receive a strong signal from the transponders.

As an additional example of calibration by reference-state measurements, the farmer might dig a hole to embed a transponder in the soil. As part of digging the hole, the farmer can collect a sample of the soil and measure the moisture content directly. With such knowledge of the current moisture content, the farmer can now perform a reference measurement of signal strength from the transponder. Signal strength from future measurements can thus be associated with changes in moisture content.

Alternative embodiments of the present invention can achieve calibration through the use of reference transponders. For example, in addition to comprising one or more transponders embedded in the material to be tested, such embodiments can comprise additional transponders that are positioned near the embedded transponders but are not coupled to the material. Such additional transponders are referred to as reference transponders.

For example, the civil engineer might place some reference transponders on the surface of the concrete structure near where embedded transponders are placed. Signal strength from the reference transponders is not affected by concrete deterioration. Therefore, the condition of the concrete can be calculated by comparing signal strength from embedded transponders with signal strength from reference transponders on the surface. The use of reference transponders can relax the requirement of repeatability of interrogator position.

DETAILED DESCRIPTION

Figure 1:
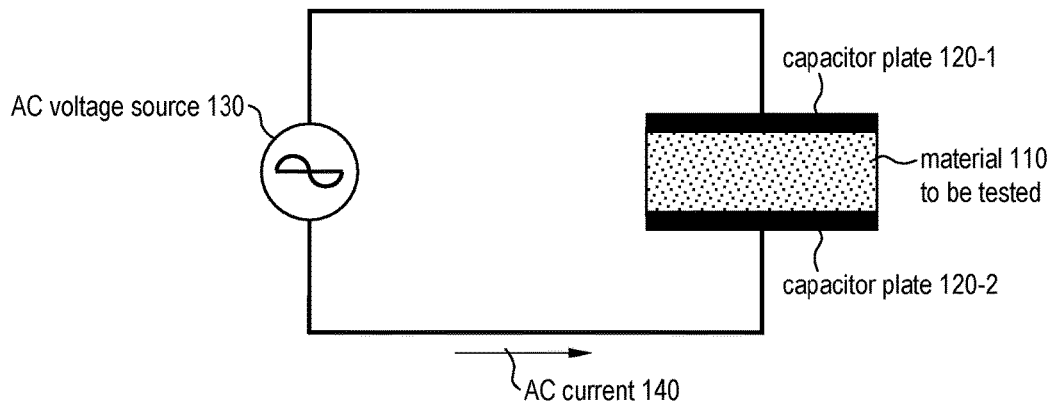
FIG. 1 depicts a technique known as impedance spectroscopy in the prior art.
Figure 2:
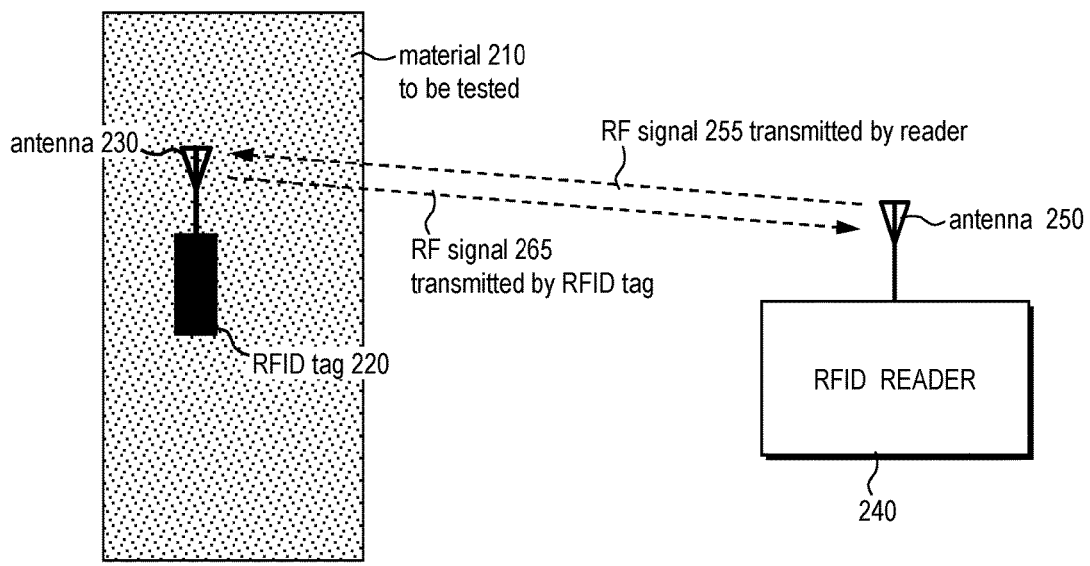
FIG. 2 depicts a system known in the prior art for performing noninvasive material testing.
Figure 3:
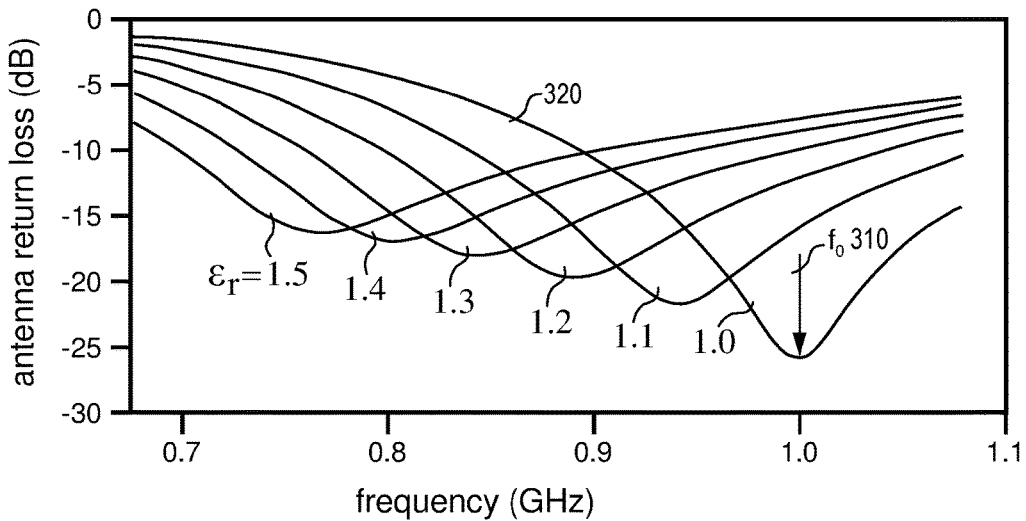
FIG. 3 is a diagram of the response of a resonant antenna coupled to a material medium. The return loss of the antenna is plotted for different values of the real part of the permittivity of the material.

FIG. 3 is a diagram of the response of a resonant antenna coupled to a material medium. For example, the antenna might be embedded in the material. Antenna response is expressed as decibels (dB) of return loss. This is way of representing antenna response is well known in the art.

The diagram shows six curves corresponding to six possible values of the real part of the permittivity. It is customary, in the art, to denote the real part of the permittivity with the symbol $\varepsilon_r$. Each of the six curves shows antenna return loss as a function of frequency for the indicated value of $\varepsilon_r$. The diagram shows clearly that antenna response is substantially affected by changes in $\varepsilon_r$. In particular, the curves were generated for a resonant antenna tuned to a resonant frequency $f_0$ of 1 GHz assuming the value $\varepsilon_r=1$ for the real part of the permittivity. Accordingly, curve 320 shows that minimum return loss occurs at the resonant frequency 310 of $f_0=1$ GHz, as expected, when $\varepsilon_r=1$.

When the value of $\varepsilon_r$ is different from the design value of $\varepsilon_r=1$, the figure shows that the minimum return loss occurs at a frequency different from the nominal resonant frequency, and that the minimum is not as low. The mathematical formulas used for deriving the curves of FIG. 3 are well known in the art.

In this disclosure, the "nominal" resonant frequency should be understood to mean the resonant frequency for which the resonant antenna was designed. In the previous paragraph, the antenna was designed for use in air, where $\varepsilon_r=1$; however, when an antenna is intended to be used in a particular material medium, the antenna designer might design the antenna for a nominal resonant frequency when the antenna is embedded in the medium. In this case, the antenna designer might use a reference value for the permittivity of the medium, with the understanding the actual resonant frequency of the antenna might change if the permittivity changes.

Figure 4:
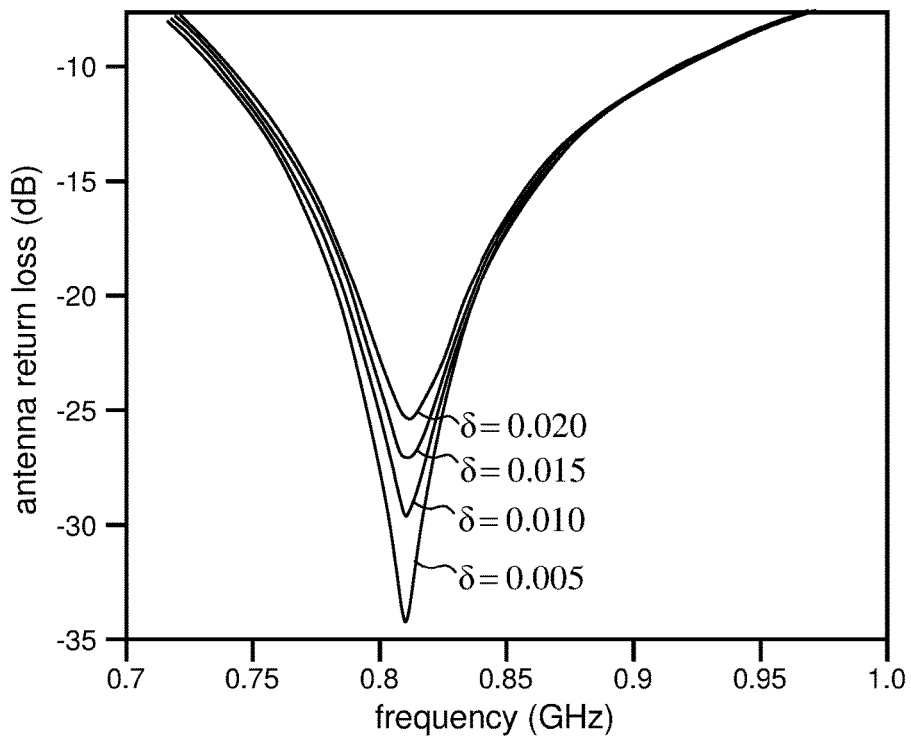
FIG. 4 is a diagram of the response of a resonant antenna coupled to a material medium. The return loss of the antenna is plotted for different values of the loss tangent of the material.

FIG. 4 also shows a diagram of the response of a resonant antenna coupled to a material medium. However, the curves in this figure show the consequences of changes in the imaginary part of the permittivity. It is customary, in the art, to express the imaginary part of the permittivity in terms of the so-called loss tangent, denoted by the symbol $\delta$. In this figure, the nominal resonant frequency of the antenna is 0.81 GHz. The figure clearly shows that changes in $\delta$ affect the depth of the minimum return loss, but the frequency of the minimum is not affected.

Those skilled in the art will recognize that the curves of FIG. 4 correspond to changes in the quality factor of the resonant antenna; lower values of $\delta$ yield a higher quality factor. As with FIG. 3, the mathematical formulas used for deriving the curves of FIG. 3 are well known in the art.

The curves in FIG. 3 and FIG. 4 show that a change in either the real or the imaginary part of the permittivity yields a change in antenna return loss. Such a change is accompanied by a change in the signal strength of a signal received, transmitted or reflected through the antenna. However a measurement of such signal strength at a single frequency does not make it possible to distinguish which of the two parts has changed.

It will be clear to those skilled in the art, after reading this disclosure, that two measurements of signal strength performed at two different frequencies are sufficient to distinguish which of the two parts has changed. Indeed, those skilled in the art will know, after reading this disclosure, how to apply the mathematical formulas used to derive the curves of FIG. 3 and FIG. 4 to obtain the values of $\varepsilon_r$ and $\delta$ from two or more signal-strength measurements performed at two or more different frequencies. The accuracy of the results will depend on the choice of the frequencies. For example, it might be desirable to choose one frequency near the nominal resonant frequency $f_0$, and another frequency away from $f_0$. If more than two measurements are available, the accuracy of the results will, in general, improve.

Figure 5:
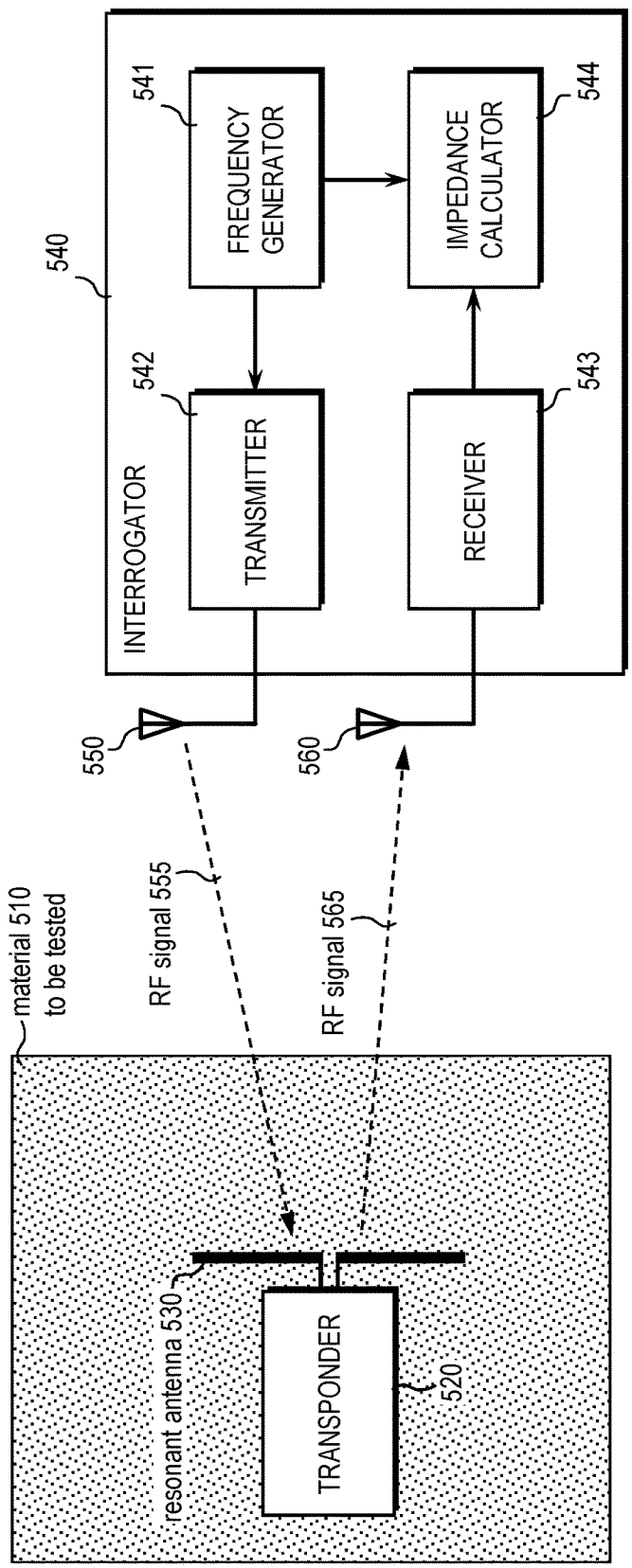
FIG. 5 depicts a system for remote measurement of both real and imaginary components of the impedance of a material in accordance with a first illustrative embodiment of the present invention.

FIG. 5 depicts a system 500 for remote measurement of both real and imaginary components of the impedance of a material in accordance with a first illustrative embodiment of the present invention. In this embodiment, transponder 520 is embedded in material 510. The system measures the real and imaginary parts of the impedance of material 510 through the use of wireless RF signals. In particular, the system comprises interrogator 540 which is capable of transmitting RF signal 555. For that purpose, interrogator 540 comprises transmitter 542, which generates RF signal 555, and antenna 550, which radiates RF signal 555 as an electromagnetic wave. The frequency of RF signal 555 is set by multiple frequency generator 541 which is coupled to transmitter 542.

RF signal 555 propagates through the free space that separates interrogator 540 from material 510, and then further propagates through material 510 itself, to reach resonant antenna 530, which is part of transponder 520 and is coupled to the transponder's circuitry. Antenna 530 is also coupled to material 510 by virtue of being embedded in it.

Transponder 520 comprises circuitry, not explicitly shown in the figure, capable of responding to RF signal 555 by generating RF signal 565. For example, transponder 520 might employ backscatter modulation for generating RF signal 565. Backscatter modulation is a technique well known in the art. With backscatter modulation, the signal strength of RF signal 565 is proportional to the signal strength of RF signal 555, as received by transponder 520. Both signal strengths also depend on the response of resonant antenna 530, which, in turn, depends on the impedance of material 510, as detailed above.

RF signal 565 is received by interrogator 540 through antenna 560 and receiver 543. The receiver is capable of measuring the signal strength of RF signal 565, as received by interrogator 540. The measured signal strength is provided to impedance calculator 544, which also has access to the frequency of RF signal 555 as generated by multiple frequency generator 541. If transponder 520 generates RF signal 565 via backscatter modulation, the frequency of RF signal 565 is, essentially, the same as the frequency of RF signal 555.

Impedance calculator 544 calculates the values of the real part and the imaginary part of the impedance of material 510 based on the measured received signal strength, on the frequency of RF signal 555, and on known parameters of resonant antenna 530, transponder 520 and the material itself. As discussed in the Summary, more than one signal-strength measurement is necessary to achieve accurate results.

To provide impedance calculator 544 with the necessary multiple measurements, multiple frequency generator 541 generates one frequency at a first time for a sufficiently long duration to enable receiver 543 to achieve an accurate measurement of signal strength. Then, at a later time, multiple frequency generator 541 generates a second frequency for a sufficiently long duration to enable receiver 543 to achieve a second accurate measurement of signal strength. How the two frequencies should be chosen was discussed in previous paragraphs.

Figure 6:
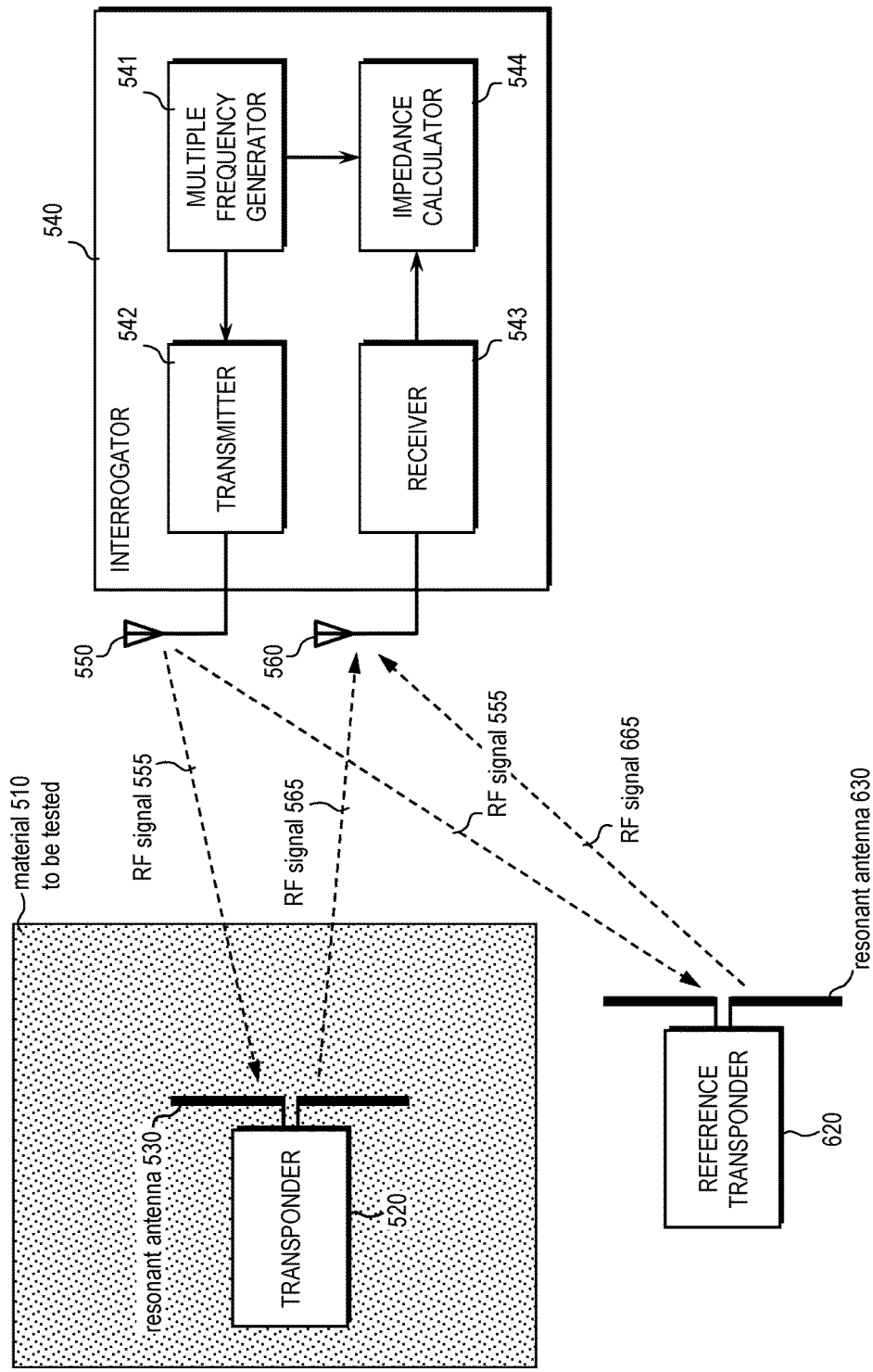
FIG. 6 depicts a system in accordance with a second illustrative embodiment of the present invention.

FIG. 6 depicts a system 600 in accordance with a second illustrative embodiment of the present invention. System 600 achieves improved accuracy, compared to system 500, through the use of reference transponder 620. In particular, system 600 comprises all the components of system 500; they perform similar functions in system 600 as in system 500. Additionally, system 600 comprises reference transponder 620, which is identical to transponder 520 but is not embedded into material 510, and its antenna 630 is, therefore, not coupled to material 510.

Reference transponder 620 is positioned in the vicinity of transponder 520, such that RF signal 555 can be received simultaneously by transponder 520 and reference transponder 620. Both transponders generate an RF signal in response to RF signal 555. RF signal 665, generated by the reference transponder, is received by the interrogator along with RF signal 565.

Receiver 543 is capable of independently measuring the signal strengths of both received RF signals. Both signal strengths are provided to impedance calculator 544. The impedance calculator knows that the reference transponder 620 is not affected by the impedance of material 510, and it knows that the reference transponder is otherwise identical to transponder 520. Therefore, the signal strength of RF signal 665 from the reference transponder can be used as a reference to estimate what the signal strength of RF signal 565 would be if material 510 were not present. The availability of the reference measurement of RF signal 665 enables impedance calculator 544 to achieve more accurate results.

Figure 7:
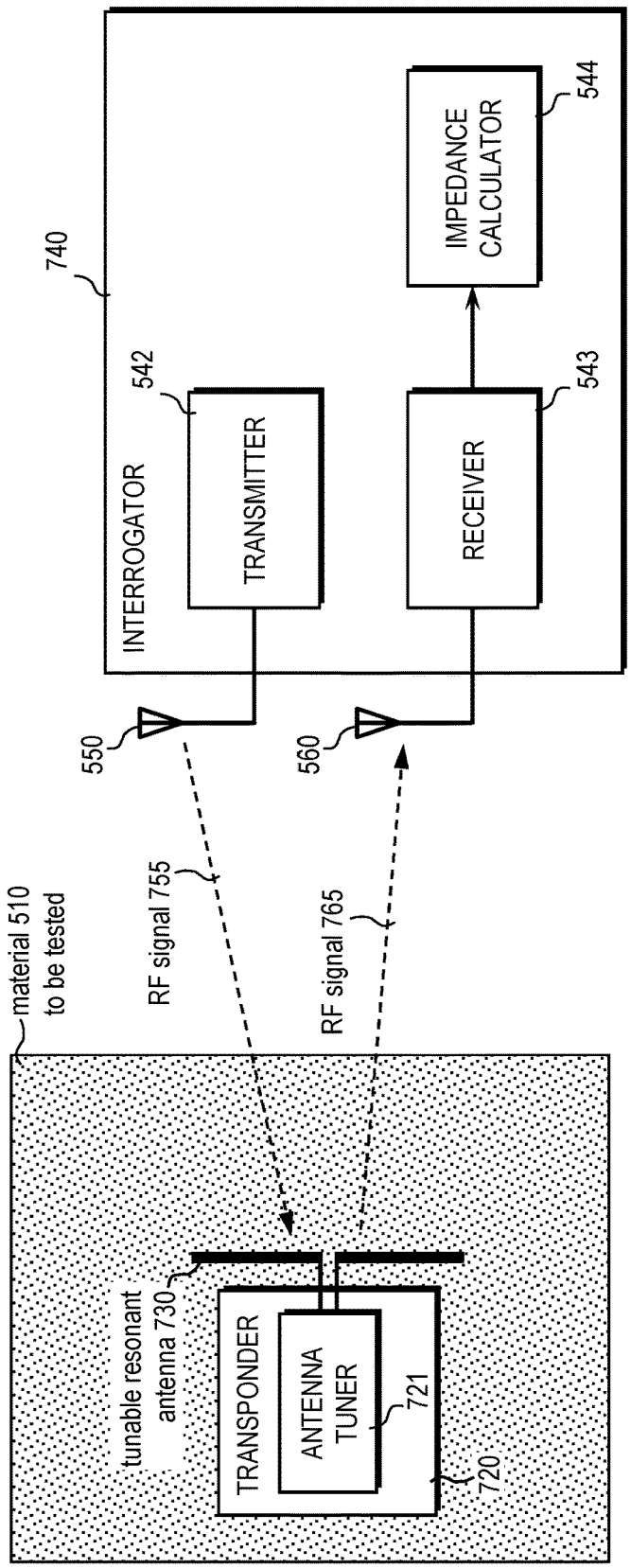
FIG. 7 depicts a system in accordance with a third illustrative embodiment of the present invention.

FIG. 7 depicts a system 700 in accordance with a third illustrative embodiment of the present invention. System 700 is useful in situations where the interrogator is not allowed to generate multiple frequencies for RF signal 555. That's why interrogator 740 in FIG. 7 does not comprise a multiple frequency generator.

Compared to system 500, system 700 comprises transponder 720 in place of transponder 520. Transponder 720 comprises an antenna tuner 721 that is capable of controlling the nominal resonant frequency of tunable resonant antenna 730.

It is well known in the art how to control the resonant frequency of an antenna. A variety of methods are available. For example, and without limitation, antenna tuner 720 might comprise a bank of capacitors and/or inductors of different values that might be connected in parallel or in series with the antenna. Different capacitance or inductance values will yield different values for the nominal resonant frequency of tunable resonant antenna 730.

Changing the nominal resonant frequency of antenna 730, while keeping the frequency of RF signal 755 constant, is equivalent to changing the frequency of the RF signal while keeping the antenna unchanged. The equivalence occurs because of the format of the mathematical formulas that describe the interaction of the antenna with the RF signal. Therefore, the operation and functionality of receiver 543 and of impedance calculator 544 in this third illustrative embodiment are similar to what they were in the first illustrative embodiment of FIG. 5, and the remarks made regarding these components in the discussion of FIG. 5 also apply here.

Figure 8:
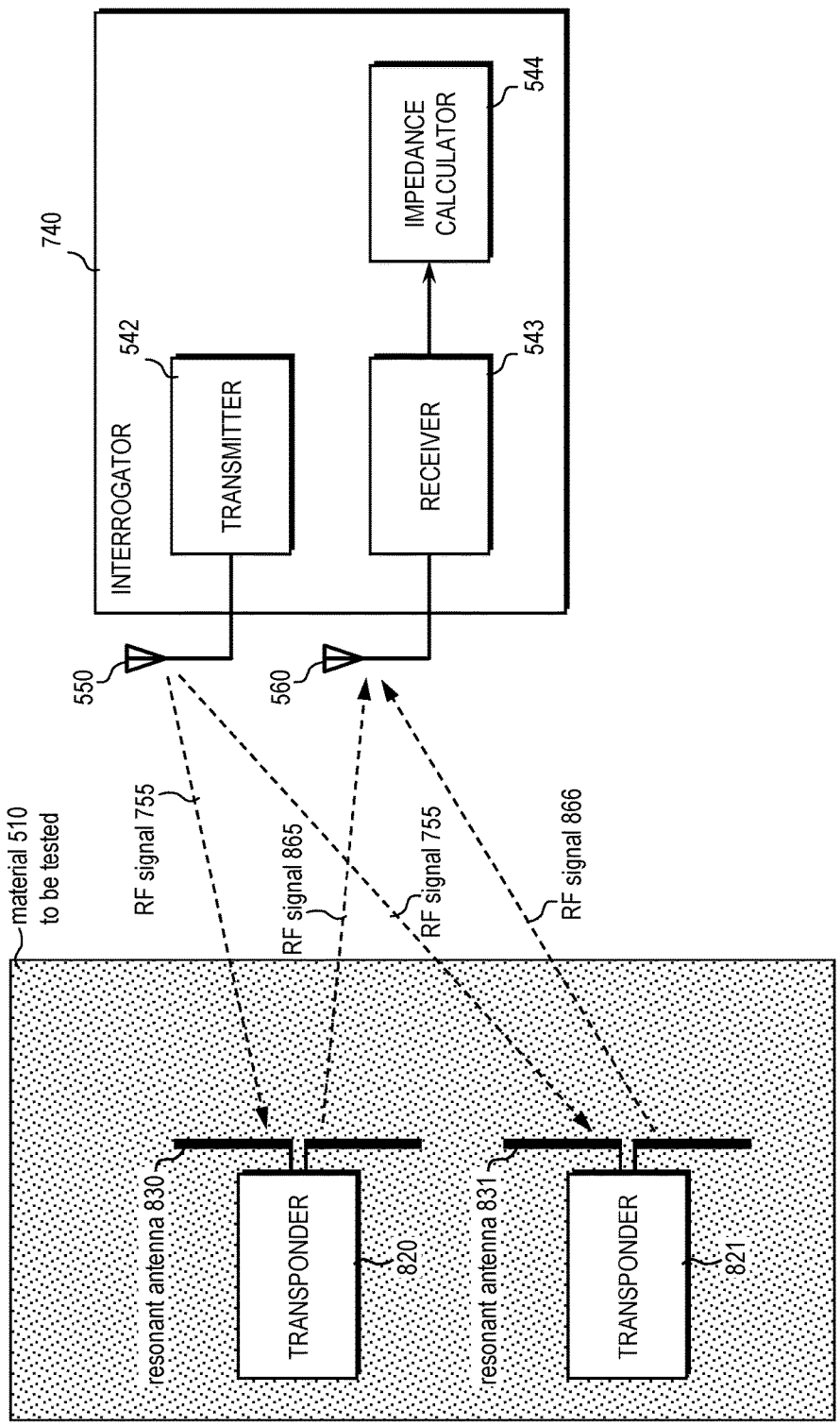
FIG. 8 depicts a system in accordance with a fourth illustrative embodiment of the present invention.

FIG. 8 depicts a system 800 in accordance with a fourth illustrative embodiment of the present invention. System 800 is similar to system 700 in that the interrogator does not change the frequency of the transmitted RF signal 755. System 800 is useful in situations where a transponder with a tunable antenna like transponder 720 is not possible or desirable. For example, the use of a capacitor bank or an inductor bank might cause transponder 720 to be too costly.

In system 800, the tunable transponder 720 is replaced by the two nontunable transponders 820 and 821 whose antennas have fixed nominal resonant frequencies chosen as needed to yield accurate results. For example, one nominal resonant frequency might be chosen to be near the frequency of RF signal 755, while the other nominal resonant frequency might be chosen to be away from the frequency of RF signal 755.

Because the two nontunable transponders are embedded in material 510 near one another, both can receive RF signal 755, and they will be similarly affected by changes in the impedance of material 510. Therefore, having the two nontunable transponders is equivalent to having the single tunable transponder 720. It will be clear to those skilled in the art, after reading this disclosure, how to exploit this equivalence in embodiments of the present invention similar to this fourth illustrative embodiment.

Figure 9:
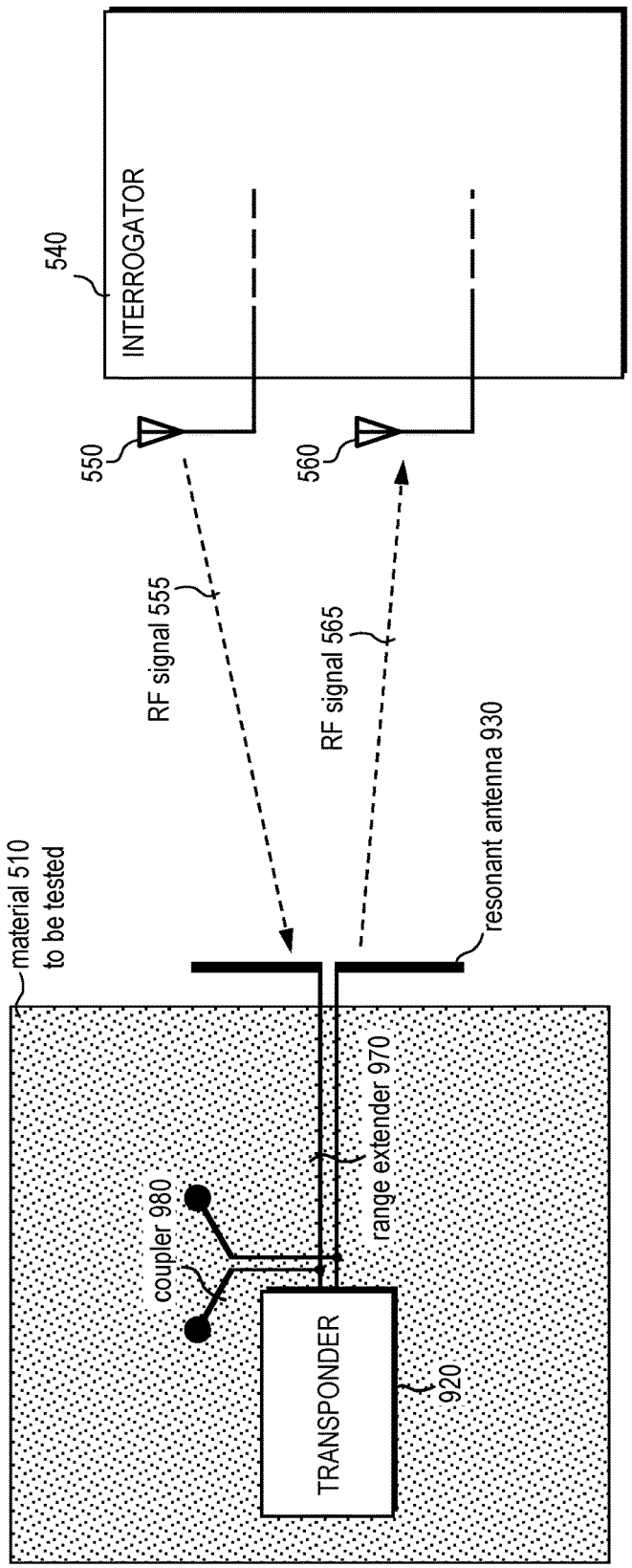
FIG. 9 depicts a system in accordance with a fifth illustrative embodiment of the present invention.

FIG. 9 depicts a system 900 in accordance with a fifth illustrative embodiment of the present invention. System 900 comprises the same interrogator as system 500, and, similarly to system 500, multiple signal strength measurements are made for different frequencies of the RF signal 555 transmitted by the interrogator In system 900, the circuitry of transponder 920 is similar to the circuitry of transponder 520, but the antenna is different. The transponder of system 900 is useful in situation where the transponder needs to be embedded deep inside the material to be tested. For example, in a bridge, it might be desirable to assess the condition of concrete deep inside the structure of the bridge. In such a case, the resonant antenna needs to be coupled to the concrete at a place that is deep inside the structure.

While it is, in principle, possible to place a transponder like transponder 520 deep inside the structure of the bridge where it is needed, there are two problems. First, propagation of RF signals through concrete is not as good as through empty space: it is possible that signal attenuation might be excessive, such that RF signal 565 becomes too weak for interrogator 540 to detect it. Second, RF signals 555 and 565 propagate through a lot of concrete whose condition affects their propagation; therefore, the signal strength of RF signal 565, as received by interrogator 540, reflects not only the condition of concrete at the spot where the transponder is placed, but also the condition of the intervening concrete, which might corrupt the results and make it difficult to assess just the condition of the concrete where the transponder is placed.

The transponder in FIG. 9 solves these problems through the use of range extender 970. The range extender, in this illustrative example, is a transmission line designed such that its electromagnetic fields are not coupled to the material in which it is embedded. It is well known in the art how to make such a transmission line. For example, and without limitation, a coaxial cable would exhibit the requisite behavior.

At one end of the transmission line, the range extender reaches the outer surface of the material. There, it is connected to a resonant antenna that is not coupled with the material and is separated from the interrogator by free space or, at least, by a propagation path characterized by low loss and not affected by the material. However, for the resonant antenna to achieve the desired result, it needs to be somehow coupled to the material in the vicinity of where transponder 920 is placed. This is accomplished by coupler 980.

Coupler 980 is a structure that generates electric and/or magnetic fields in the material. For example, coupler 980 might be itself a resonant antenna coupled with the material similar to antenna 530. However, whereas an antenna is optimized for radiating an electromagnetic wave, this is not a requirement for coupler 980. It is just necessary that coupler 980 be well coupled to the material such that its impedance is affected by the impedance of the material. In FIG. 9, coupler 980 is depicted differently from the antennas depicted in this and other figures to highlight its different function; however, in some embodiments of the present invention, coupler 980 might well be identical to some of the antennas discussed in this disclosure.

Coupler 980 is coupled to the material at the place where it is desired to test the material. In order for coupler 980 to affect the response of resonant antenna 930, it must be somehow coupled to it. This is accomplished, in this illustrative embodiment, by connecting coupler 980 to the other end of range extender 970. The interaction between coupler 980 and the resonant antenna 930 through range extender 970 achieves the desired coupling between resonant antenna 930 and the material. It will be clear to those skilled in the art, after reading this disclosure, how to design a specific shape of coupler 980 and how to model the behavior of resonant antenna 930, as coupled to coupler 980, so as to enable impedance calculator 544 to yield the desired results.

Although coupler 980 is depicted in FIG. 9 as being directly connected to range extender 970, it will be clear to those skilled in the art, after reading this disclosure, ho to make and use embodiments of the present invention wherein coupler 980 is coupled to range extender 970 by other means. For example and without limitation, it might be coupled via components such as capacitors or inductors, or even via electromagnetic coupling by simply placing it in the vicinity of range extender 970 with appropriate conductive patterns to achieve the desired mutual coupling. The only requirement is that coupler 980 be coupled to range extender 970 in such a way that the impedance of the material affects the response of the resonant antenna.

In some of the illustrative embodiments presented in this disclosure, two or more transponders can transmit a signal at the same time. it is well known in the art how to design a receiver that can receive those two simultaneous signals and measure the two signal strengths independently and accurately. For example, with backscatter modulation, the two signals might be modulated with different patterns that enable the receiver to detect them separately.

In some of the illustrative embodiments presented in this disclosure, certain actions or events are described as occurring at certain times. It should be understood that the word "time" is not intended to just denote a time instant, rather, it should be understood to refer to an "occasion" that might be an instant or might also be, for example, an extended time interval.

It will be clear to those skilled in the art, after reading this disclosure, that the individual features of the illustrative embodiments presented in this disclosure can be combined in a variety of ways to yield alternative embodiments of the present invention that are not explicitly presented in this disclosure. For example, and without limitation, the benefits of using a reference transponder that were presented in conjunction with the second illustrative embodiment of FIG. 6 can be also enjoyed by other illustrative embodiments simply by adding a reference transponder to those embodiments.

It is to be understood that this disclosure teaches just one or more examples of one or more illustrative embodiments, and that many variations of the invention can easily be devised by those skilled in the art after reading this disclosure, and that the scope of the present invention is defined by the claims accompanying this disclosure.

What is claimed:

1. An apparatus for sensing a wave impedance of a material, the apparatus comprising:

an interrogator including at least one interrogating antenna, a transmitter, a receiver, and an impedance calculator, wherein the transmitter transmits a first radio-frequency (RF) signal and the impedance calculator determines the wave impedance of the material;

a transponder, wherein the transponder generates a second RF signal responsive to the first RF signal, wherein the second RF signal is received by the receiver;

a range extender that is electrically connected to the transponder, and wherein the range extender does not electromagnetically couple to the material;

a first resonant antenna, wherein the first resonant antenna is not disposed in the material and is electrically connected to the range extender; and a coupler, wherein the coupler is at least one of either electrically connected or magnetically coupled to the range extender, and wherein the coupler generates at least one of an electrical, electromagnetic, or a magnetic field in the material, and further wherein the at least one field couples to the material such that an electrical impedance of the coupler is affected by the material, wherein:

the transponder and the coupler are embedded in the material.

2. The apparatus of claim 1 wherein the range extender comprises a transmission line.

3. The apparatus of claim 1 wherein the coupler is tunable.

4. The apparatus of claim 3 wherein the interrogator and the coupler are tuned to different frequencies.

5. The apparatus of claim 1 wherein the coupler is a second resonant antenna.

6. The apparatus of claim 1 wherein the coupler comprises multiple antennas tuned to one or more frequencies.

7. The apparatus of claim 1 wherein the material blocks wireless communications between the coupler and the first resonant antenna.

8. The apparatus of claim 1 wherein the first resonant antenna is tunable.

9. The apparatus of claim 8 wherein the interrogator and the first resonant antenna are tuned to the same frequency.

10. The apparatus of claim 1 wherein the interrogator further comprises a frequency generator.

11. The apparatus of claim 9 wherein the receiver measures a signal strength of the second RF signal.

12. The apparatus of claim 11 wherein the impedance calculator calculates the wave impedance based on the signal strength of the second RF signal and a frequency of the first RF signal.

13. The apparatus of claim 1 wherein impedance calculator calculates complex wave impedance.

14. The apparatus of claim 1 wherein the interrogator is disposed in an unmanned vehicle.

15. The apparatus of claim 1 wherein the transponder is an RFID device.

16. A method for sensing a wave impedance of a material, the method comprising:

embedding a transponder within the material, wherein the transponder generates a second RF signal responsive to a first RF signal generated by an interrogator that is not within the material;

embedding a coupler within the material, wherein the coupler generates at least one of an electric, electromagnetic, or magnetic field in the material, and further wherein the at least one field couples to the material such that an electrical impedance of the coupler is affected by the material;

electrically connecting a range extender to the transponder, wherein the range extender does not electromagnetically couple to the material and wherein the range extender extends outside of the material;

forming a first operative coupling between the material, the transponder, and the coupler;

forming a second operative coupling between the transponder and a first resonant antenna that is not within the material; and forming a third operative coupling between the interrogator and the first resonant antenna, wherein:

a first RF signal is transmitted from the interrogator to the transponder via the third operative coupling and the second operative coupling; and a second RF signal is transmitted from the transponder to the interrogator via the second operative coupling and the third operative coupling, wherein the second RF signal is generated by the transponder responsive to the first RF signal, and wherein a signal strength of the first RF signal and the second RF signal are dependent, in part, on the wave impedance of the material, due to the first operative coupling.

17. A method for sensing a wave impedance of a material, the method comprising:

embedding a transponder within the material;

embedding a coupler within the material, wherein the coupler generates at least one of an electric, electromagnetic, or magnetic field in the material, and further wherein the field couples to the material such that an electrical impedance of the coupler is affected by the material;

electrically connecting a range extender to the transponder, wherein the range extender does not electromagnetically couple to the material and wherein the range extender extends outside of the material;

transmitting, by an interrogator, a first radio-frequency (RF) signal at a first frequency;

receiving, by the transponder, through a resonant antenna that is not within the material but that is electrically connected to the range extender, the first RF signal;

generating, by the transponder, a second RF signal based on the first RF signal;

receiving, by the interrogator, the second RF signal;

measuring a first signal strength of the second RF signal, as received by the interrogator;

calculating the wave impedance of the material based on the signal strength of the second RF signal and a frequency of the first RF signal.

18. An apparatus for sensing a wave impedance of a material, the apparatus comprising:

an interrogator including at least one interrogating antenna, a transmitter, a receiver, and an impedance calculator, wherein the transmitter transmits a first radio-frequency (RF) signal and the impedance calculator determines the wave impedance of the material;

a transponder, embedded in the material, wherein the transponder generates a second RF signal responsive to the first RF signal;

a first resonant antenna, wherein the first antenna receives the second RF signal and transmits it to the receiver, wherein the first resonant antenna is not disposed in the material; and an operative coupling for propagating the second RF signal between the transponder and the first resonant antenna, and wherein the operative coupling does not couple to the material.

* * * * *